United States Patent [19]

López

[11] Patent Number: 5,500,352
[45] Date of Patent: Mar. 19, 1996

[54] MEMBRANE FILTRATION PROCESS FOR 6-AMINOPENICILLANIC ACID

[75] Inventor: Jorge L. López, Natick, Mass.

[73] Assignee: Sepracor, Inc., Marlborough, Mass.

[21] Appl. No.: 36,327

[22] Filed: Mar. 24, 1993

[51] Int. Cl.$^6$ .............................. C12P 37/06; C12N 9/84
[52] U.S. Cl. .................... 435/44; 435/230; 435/813
[58] Field of Search .............................. 435/44, 230, 813

[56] References Cited

U.S. PATENT DOCUMENTS

| | | | |
|---|---|---|---|
| 3,161,573 | 12/1964 | Godtfredsen | 435/44 |
| 3,615,024 | 8/1968 | Michaels | 210/490 |
| 3,887,432 | 6/1975 | Cawthorne | 435/44 |
| 4,033,817 | 7/1977 | Gregor | 435/44 |
| 4,371,612 | 2/1983 | Matsumoto et al. | 435/44 |
| 4,664,808 | 5/1987 | Kim | 210/638 |
| 4,800,162 | 1/1989 | Matson | 435/280 |

FOREIGN PATENT DOCUMENTS

| | | | |
|---|---|---|---|
| 0742059 | 1/1970 | Belgium | 435/44 |
| 0082097 | 5/1984 | Japan | 435/44 |

OTHER PUBLICATIONS

Ryu et al. "Microbial Penicillin Amidohydrolase and the Performance of a Continous Enzyme Reactor System" *Proc. IV IFS: Ferment. Technol. Today*, 307–314 (1972).

J. Bryjak & A. Noworyta, "Enzyme Membrane Bioreactor for Hydrolysis of Penicillin G", *Biochem. Eng.—Stuttgart*, [Proc. Int. Symp.], 2nd, Meeting (1990) 122–5. Edited by: Reuss, Matthias. Fischer: Stuttgart, Fed. Rep. Ger.

Giacobbe et al., "Production of 6APA in the Penicillin G Fermentation Plant by Using Fiber–Entrapped Penicillin Amidase", *Enzyme Eng.*, 4, 245–252 (1978).

Barenschee et al. "Possibilities of Liquid Membrane Technology for Immobilisation of Enzymes" *Chem. Ing. Tech.* 61, 426–427 (1989).

Tiskas et al. "Hohlfasergestützte Flüssigmembranen zur Extraktion . . . " *Chem. Ing. Tech.* 64, 545–548 (1992).

Michaels et al. "Membranes in Biotechnology: State of the Art" *Desalination* 53, 231–258 (1985).

Veronese et al. "Immobilization of Purified Penicillin Acylase in a Polarized Ultrafiltration Membrane Reactor" *Ann. N.Y. Acad. Sci. 434* (Enzyme Eng.) 127–130 (1984).

*Primary Examiner*—Herbert J. Lilling
*Attorney, Agent, or Firm*—Heslin & Rothenberg

[57] ABSTRACT

The invention relates to an improved process for converting 6-acylaminopenicillanic acid (6-AAPA) to 6-aminopenicillanic acid (6-APA). The process employs a solution or suspension of penicillin acylase from which the product is separated after reaction by ultrafiltration through a particular class of polymer membranes. The process of the invention may also be applied to the production of 7-aminodesacetoxycephalosporanic acid (7-ADCA) and can be incorporated into an improved, streamlined process for obtaining 6-APA from fermentation broths.

18 Claims, 2 Drawing Sheets

MEMBRANE FILTRATION PROCESS FOR 6-AMINOPENICILLANIC ACID

FIELD OF THE INVENTION

The invention relates to a process for converting 6-acylaminopenicillanic acid (6-AAPA) to 6-aminopenicillanic acid (6-APA) or 7-acylaminodesacetoxycephalosporanic acid (7-AADCA) to 7-aminodesacetoxycephalosporanic acid (7-ADCA).

BACKGROUND OF THE INVENTION

Most semisynthetic β-lactam antibiotics are prepared by reaction of 6-aminopenicillanic acid (6-APA) or 7-aminodesacetoxycephalosporanic acid (7-ADCA) with the required side-chain precursor. 6-APA is typically produced by enzyme based hydrolysis of either benzyl penicillin (PenG) or phenoxymethyl penicillin (PenV). 7-ADCA is prepared by enzymatic hydrolysis of cephalosporin G, which is available by ring expansion of PenG.

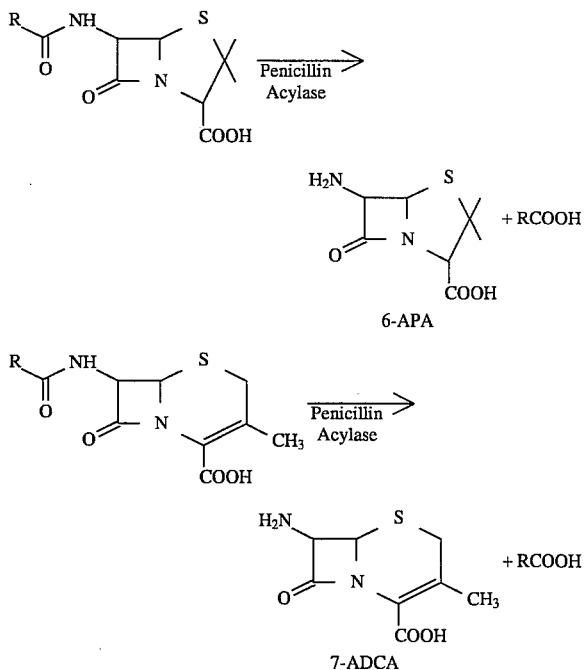

PenG: R = PhCH$_2$—
PenV: R = PhOCH$_2$—
CephG: R = PhCH$_2$—

Enzyme processes used for the manufacture of 6-APA or 7-ADCA rely on the use of enzyme which has been immobilized on a suitable support. This makes separation of the reaction products from the biocatalyst a simple procedure. The reaction is carried out in aqueous media at elevated temperatures (e.g. 28°–37° C.). Several different reactor configurations have been described in the literature, with stirred tank reactors and packed bed reactors being the most popular. In almost all cases, the enzyme is immobilized on an inert support of some type so that it can be used for multiple batches. In the case of the stirred tank batch reactor, substrate penicillin (in the form of its potassium salt) is charged to a large vessel containing the immobilized enzyme. The reaction pH is maintained in the desired range through the controlled addition of a weak base such as dilute ammonium hydroxide or caustic. The reaction is allowed to proceed to 95–99% conversion, at which point the immobilized enzyme is filtered off and the 6-APA/acid/water filtrate discharged to a downstream recovery operation. The crystalline 6-APA product is precipitated by the addition of inorganic acid and recovered by simple filtration and drying. The phenylacetic acid (in the PenG case) or the phenoxyacetic acid (in the case of PenV) is extracted into an organic solvent and recycled back upstream in the process to the penicillin fermentation step. These immobilized enzyme processes have been in use for over 20 years.

In the early development of commercial 6-APA processes, the need to immobilize the enzyme was necessitated in part by the cost of the enzyme which had to be reused many times in order to make its cost contribution to the final product as low as possible. By immobilizing the enzyme on a solid support, the separation of the aqueous product solution from the catalyst became simply a matter of passing the reactor contents through filters capable of retaining the enzyme support. The size difference between the products and the catalyst is in the order of $10^5$ when the catalyst is immobilized, so that crude filters would suffice.

More recently it has been recommended that enzymes be immobilized on the surface of an ultrafiltration membrane. See, for example, European patent 69869, U.S. Pat. No. 4,800,162 and Bryjak and Noworyta [*Biochem. Eng.— Stuttgart, Proc. Int. Symp. 2nd* 1990, 122–125 ed. Reuss; Fischer Stuttgart (1991)]. The process is operated such that product ultrafiltration is done on a continuous basis. The major flaw in this configuration is that the rate of continuous addition of substrate must be relatively small to ensure that high conversions are obtained. This type of configuration is called a Continuous Stirred Tank Reactor (CSTR). To overcome the limitations of the CSTR configuration, a number of tanks are connected in series, which requires more tanks, membrane area, pumps, and pH control equipment.

While these approaches offer certain advantages, drawbacks remain: (1) there is always some, and often much, inactivation of the enzyme as a result of the immobilization chemistry; (2) pH control and diffusion resistance become significant concerns because of restricted access to the enzyme; (3) a considerable volume of the reactor is consumed by the inert carrier; and (4) immobilization often requires expensive chemistry, more time and more sophisticated equipment. There is thus a need for a process that minimizes or eliminates the foregoing drawbacks.

SUMMARY OF THE INVENTION

It is an object of the present invention to provide a process for producing 6-APA and 7-ADCA that can be carried out with free enzymes in solution.

It is a further object to provide a process for producing 6-APA or 7-ADCA in high yield with a minimum of expensive equipment.

It is a further object to provide a process for producing 6-APA or 7-ADCA in high yield using a minimum of penicillin acylase.

Ultrafiltration membranes, if they meet certain criteria, provide the basis for an improved process. Ultrafiltration membranes are generally used to separate high molecular weight species from low molecular weight ones. Many types of these are available commercially with a wide range of molecular weight cutoffs. Molecular weight cutoff is typically defined as the molecular weight over which species will be rejected, i.e., a 50,000 molecular weight cutoff membrane will reject molecules with molecular weights equal to or greater than this value. Enzymes are typically characterized by molecular weights in excess of 20,000. Therefore, an ultrafiltration with a MW cutoff of 20,000 can be used as an efficient means of separating the enzyme from reaction participants assuming that these have a sufficiently low molecular weight, e.g., less than 1000.

There appear to be no reports in the literature of processes for the production of 6-APA and 7-ACDA by free solutions of penicillin acylase followed by separation of the product via ultrafiltration membranes and reuse of the enzyme solution in a cycling process.

The present invention relates to a process for producing 6-aminopenicillanic acid (6-APA) from a 6-acylaminopenicillanic acid (6-AAPA) comprising the steps of:

(a) supplying to a reaction vessel a solution or suspension of 6-AAPA or a salt thereof;

(b) supplying, from a first side of a membrane filter having a first and a second side, a solution or suspension of penicillin acylase to said reaction vessel;

(c) circulating the suspension or solution of 6-AAPA and penicillin acylase to produce a homogeneous solution or a uniform suspension at pH 7.0 to 9.0 and 20° to 40° C.;

(d) continuing circulating the solution or suspension until the 6-AAPA is substantially completely converted to a solution of 6-APA; and (e) filtering the solution of 6-APA through the membrane filter until at least 90% of the 6-APA has passed to the second side of the membrane filter, while less than 10% of the penicillin acylase has passed from the first side to the second side.

In one embodiment step (b) is carried out by circulating the solution or suspension of 6-AAPA from the reaction vessel over a first side of a membrane filter having a first side and a second side, whereby the solution or suspension of 6-AAPA is brought into contact with a penicillin acylase in suspension or solution.

The same process may be used to produce 7-aminodesacetoxycephalosporanic acid from a 7-acylaminodesacetoxycephalosporanic acid.

Acyl, as used in acylaminopenicillanic acid and acylaminodesacetoxycephalosporanic acid, refers to an organic residue terminating in the C=O functionality; acylamino compounds are thus organic amides. Common acyl groups found in known penicillins include:

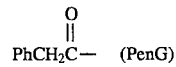
(PenG)

and

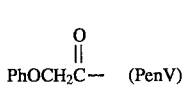
(PenV)

but any acylamino function that is a substrate for an acylase enzyme would function in the process of the invention. Penicillin acylase is also known as penicillin amidase.

A preferred 6-AAPA solution or suspension is a 5 to 10% solution of potassium benzyl penicillin, which is circulated at about pH 7.5 to 8.5 and about 25° to about 30° C. in the presence of about 10 to about 2000 units of penicillin acylase per gram of potassium benzyl penicillin. Another preferred 6-AAPA solution or suspension is a 5 to 10% solution of phenoxymethyl penicillin.

A preferred membrane for use in the process of the invention is an anisotropic hollow fiber or flat sheet membrane of polyacrylonitrile having a cutoff of 10 to 100 kdaltons.

The invention further relates to an integrated process for producing 6-aminopenicillanic acid (6-APA) from a fermentation broth comprising the steps of:

(a) acidifying a clarified fermentation broth containing a 6-acylaminopenicillanic acid (6-AAPA) or salt thereof;

(b) extracting the 6-AAPA into a suitable water-immiscible organic solvent;

(c) extracting the 6-AAPA from the water immiscible organic solvent into an alkaline aqueous solution;

(d) circulating the alkaline aqueous solution of 6-AAPA through a first hydrophilic membrane filter having a cutoff of 10 to 100 kdaltons to produce a clear aqueous filtrate substantially free of a water-immiscible solvent phase and substantially free of proteinaceous contaminants;

(e) combining the clear aqueous filtrate with an aqueous solution or suspension of penicillin acylase at pH 7.0 to 9.0 and at 20° to 40° to provide a homogeneous mixture of 6-AAPA and penicillin acylase;

(f) allowing the 6-AAPA and penicillin acylase to react until the solution of 6-AAPA is substantially completely converted to a solution of 6-APA; and (g) filtering the solution of 6-APA through a membrane filter whereby at least 90% of the 6-APA in the solution is passed through the membrane while less than 10% of the penicillin acylase passes through the membrane.

The water-immiscible solvent in some embodiments may be butyl acetate, amyl acetate or methyl isobutyl ketone.

A preferred first hydrophilic membrane is an anisotropic polyacrylonitrile hollow fiber ultrafiltration membrane. A preferred membrane has a cutoff of 25 to 50 kdaltons.

A preferred 6-acylaminopenicillanic acid salt is potassium benzyl penicillin, and the clear aqueous filtrate is a 5 to 10% solution of potassium benzyl penicillin which is then combined with about 10 to 2,000 units, preferably about 125 units, of penicillin acylase per gram of potassium benzyl penicillin at about pH 7.5 to 8.5 and about 25° to about 30° C.

A preferred acylaminodesacetoxycephalosporanic acid is 7-(2-phenylacetamido)desacetoxy cephalosporanic acid.

DETAILED DESCRIPTION OF THE INVENTION

The present invention is based on the use of membranes to separate reaction products from the catalyst. The membranes used are able to differentiate between chemical species where the size difference is only a factor of 5. A 25 kdalton protein has a Stokes-Einstein diameter of about 50 Å whereas a molecule like 6-APA has a diameter of about 10 Å. Given the size discrimination capacity of these membranes, the need to attach an enzyme to a solid support in order to facilitate its separation from the reaction product can be eliminated. The effective implementation of ultrafiltration membranes in any specific system will depend on the choice of membrane, enzyme, and nature of the reaction participants.

There are several advantages to using the enzyme in a free unimmobilized form:

(1) the pH gradients typically present in enzyme-containing particles used in unbuffered systems are eliminated;

(2) diffusional resistances within the catalyst are eliminated;

(3) no activity is lost as a result of the immobilization chemistry;

(4) due to the small size of the catalyst the total amount of catalyst that can be used in a reactor is significantly increased. The simplicity of adding make-up enzyme allows a more constant conversion to be achieved; and (5) specialized reactor and mixing equipment are not required.

To realize these advantages, a membrane-based process must satisfy the following requirements:

(1) the membrane must provide a high level of enzyme rejection;

(2) enzyme rejection must be maintained for many consecutive batches;

(3) the membrane must be mechanically stable in order to withstand the multiple ultrafiltration cycles it will go through; and (4) the membrane material must be such that it does not promote loss of activity of the enzyme when exposed to it.

Various types of membranes were evaluated to determine whether the above mentioned requirements could be satisfied. Hydrophilic membranes are generally superior to membranes having hydrophobic surfaces because there is less membrane fouling from nonspecific protein binding. It was discovered that regenerated cellulose membranes had very good rejection properties but after 25–50 batches some hollow fibers would break and allow the enzyme to leak out of the reactor system. Polyacrylonitrile membranes were found to be the most suitable. In a typical reactor run, 100 consecutive batches could be carried out with a PenG conversion of 98% or more.

Anisotropic membranes are well-known in the art (cf. U.S. Pat. No. 3,615,024) and anisotropic polyacrylonitrile (PAN) membranes are commercially available; for example PAN membranes from Asahi Medical Co., Ltd., Tokyo, Japan and from Hospal Medical Corporation, East Brunswick, N.J. have been found useful in the process of the invention. The membranes must be removed from their manufacturer-supplied packaging and mounted in solvent resistant housings.

Figure 1:
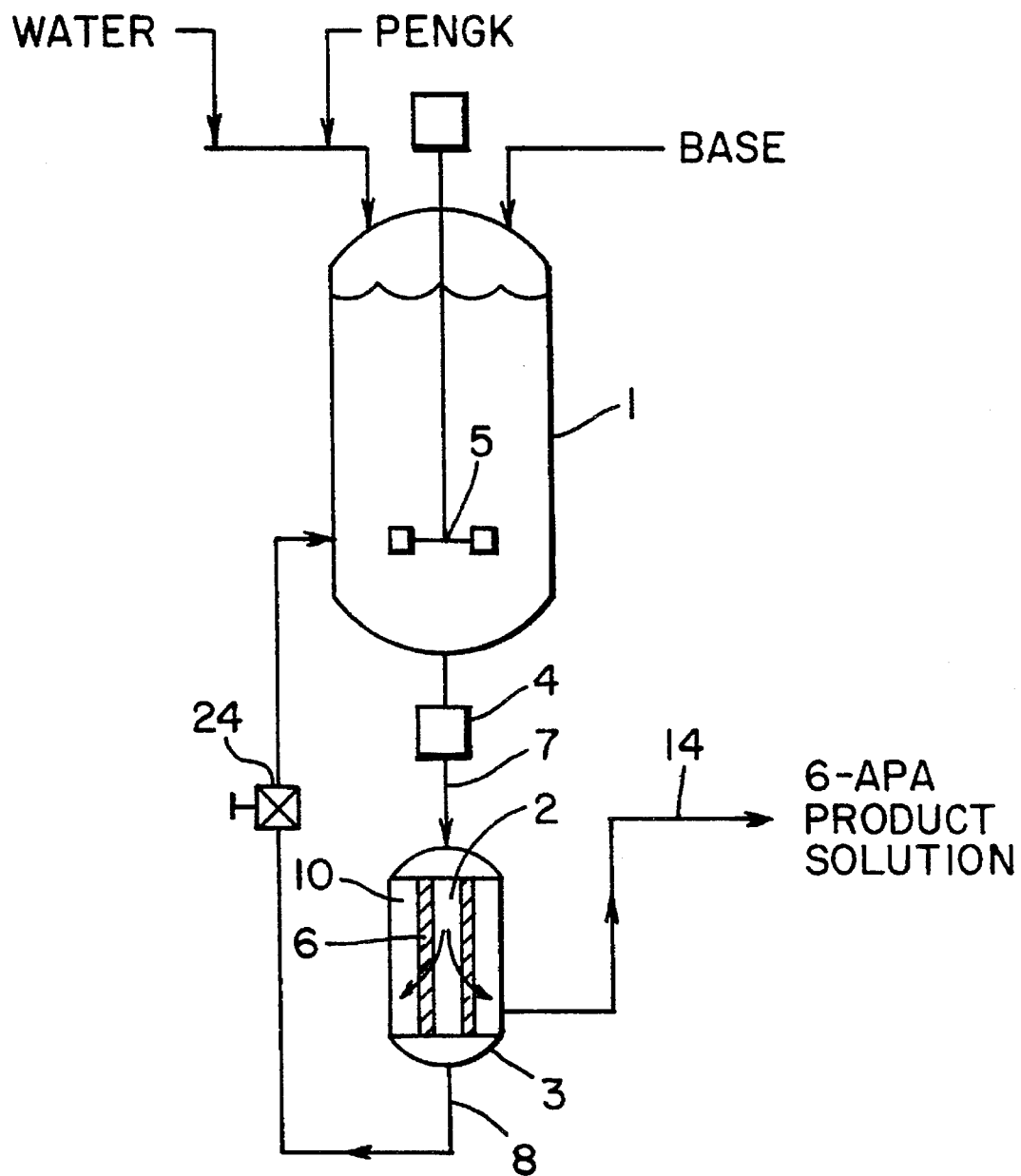
FIG. 1 is a schematic drawing of an apparatus for the practice of a process of the invention.

The operation of a 3-liter reactor proceeds as shown in FIG. 1. At the beginning of a batch, enzyme is present in the reactor tank 1 and on the lumen side 2 of the membrane module 3. The reactor tank is filled with PenGK substrate solution (8% w/w PenGK in water). After the tank is filled, a low shear pump 4 begins to recirculate the PenGK solution from the reactor tank to the membrane module 3 (lumen side or first side) and back to the reactor tank. Solution does not pass from the lumen side to the shell side 10 (or second side) of the membrane 6. During this process additional enzyme is picked up from the module and thoroughly mixed with the substrate. The enzyme is ultimately homogeneously distributed in the substrate volume. Persons of skill in the art will recognize that two membranes, each capable of retaining 70% of the acylase enzyme could be plumbed in series to retain 91% of the enzyme. Thus, while certainly not preferred for commercial reasons, the use of the basic process described above with multiple membranes in series is encompassed by the term "filtering through a membrane filter whereby less than 10% of the penicillin acylase passes through the membrane."

The pH is controlled at 7.0 to 9.0 by addition of 5N $NH_4OH$ and temperature is maintained at 20°–40° C., both by conventional apparatus not shown. An agitator 5 is provided to ensure thorough mixing of the base with the substrate/enzyme solution and to maintain appropriate heat transfer. The mixing time is commonly 3 to 4 hours and the enzyme concentration is preferably 1,000–50,000 units/liter (1 unit is the amount of enzyme required to produce 1 μmole of 6-APA per minute). At the conclusion of the enzymation step the pressure in the recirculation loop is raised to about 15 psi by means of a throttling valve 24 and product solution is ultrafiltered through the membrane 6 leaving behind an enzyme concentrate.

The enzymic cleavage can be carried to whatever extent is desired. For commercial processes, at least 90% conversion is desirable and "substantially complete" conversion implies 90% or greater.

The process and apparatus of the invention have the particular advantage of being able to run up to ten times longer between maintenance cycles because "topping-off", solutions are of much lower volume than those in immobilized enzyme systems. All enzyme based processes are subject to catalyst deactivation. With immobilized enzymes, as well as with the present invention, periodical catalyst top-off is required to maintain constant activity in the bioreactor. However, the physical size of the supporting beads usually limits the total amount of top-off which can be added in immobilized enzyme processes. The maximum routinely feasible enzyme loading on a bead is about 0.1 g enzyme/g of support. This means that 10 times more biocatalyst can be added per cycle using free enzymes than using beads in conventional immobilized enzyme reactors.

The operation of the membrane module can be considered in somewhat more detail. Entering the module at input conduit 7, the fluid divides into two paths, referred to as the shell and lumen paths (as shown in FIG. 1). The lumen path is followed by that portion of the feed fluid that does not pass through the membrane but that flows out the module through the lumen outlet 8 still carrying its original amount of enzyme. This undepleted fluid returns to the reactor tank 1 for recycling. The shell path is used to describe the path of the fluid entering the membrane module which is urged through the membrane wall 6 by the pressure differential. This fluid emerges from the shell-side surface 10 of the membrane devoid of enzyme but containing the hydrolysis product. The product stream is drawn off through conduit 14.

Although the preferred process circulates the 6-APA solution through the lumen of the membrane during hydrolysis, the enzyme could be rinsed out of the lumen and into the reactor tank after each cycle and then the hydrolysis carried out solely within the tank. The continuous circulation is done for mechanical simplicity.

EXAMPLE 1

A 1.6L aqueous solution containing 120 g of PenGK was charged to a 3 L flask provided with an air driven mixer, temperature sensor, pH probe, ammonium hydroxide addition tube, heater and an outlet to a membrane filter module. The mixture was heated and circulated through the lumen path of a membrane filter; when the temperature reached 25° C., 130 mL of a solution of penicillin acylase was added (15000 units). The starting pH of the solution was 7.0 and the pH was maintained at 8.5 throughout the reaction. After 2.5 hours and the addition of 104 mL of 3.8M $NH_4OH$, the circulation of the solution was restricted by a throttling valve downstream of a hollow fiber polyacrylonitrile filter having a 25 kdalton cutoff. At 12 to 13 psi backpressure 1.5 liters of solution containing 61 g of 6-APA were collected. The membrane was washed with 200 mL of wash and another 3 g were obtained.

As described above, the substrate to the reactor is typically the potassium salt of penicillin G, penicillin V or cephalosporin G. This solid form can be obtained from commercial producers. A typical process for making Penicillin G or V is described below:

STEP

1. Fermentation: convert nutrients to Penicillin
2. Filter microorganism (mycelia)
3. Acidify the filtered fermentation broth
4. Extract the acid into a suitable water immiscible organic solvent
5. Back extract the acid from the organic phase into an alkaline aqueous solution
6. Acidify the new aqueous solution
7. Extract the acid into fresh organic solvent
8. Add potassium acetate to the organic phase and chill it to precipitate the penicillin as the potassium salt
9. Filter the solids
10. Dry The aqueous solution obtained from step 5 above typically contains entrained solvent and some proteins from the fermentation broth. Typical solvents for this process are butyl acetate, amyl acetate, and methyl isobutyl ketone (MIBK). This process stream can be easily integrated with the unimmobilized 6-APA process described above by ultrafiltering the crude feedstream through the same type of membrane used to separate the enzyme from the product solution. Due to its hydrophilic nature the membrane will reject entrained, water-immiscible solvent. The fact that this is an ultrafiltration membrane will also provide for a means to remove contaminating proteins which would otherwise accumulate in the reactor.

Figure 2:
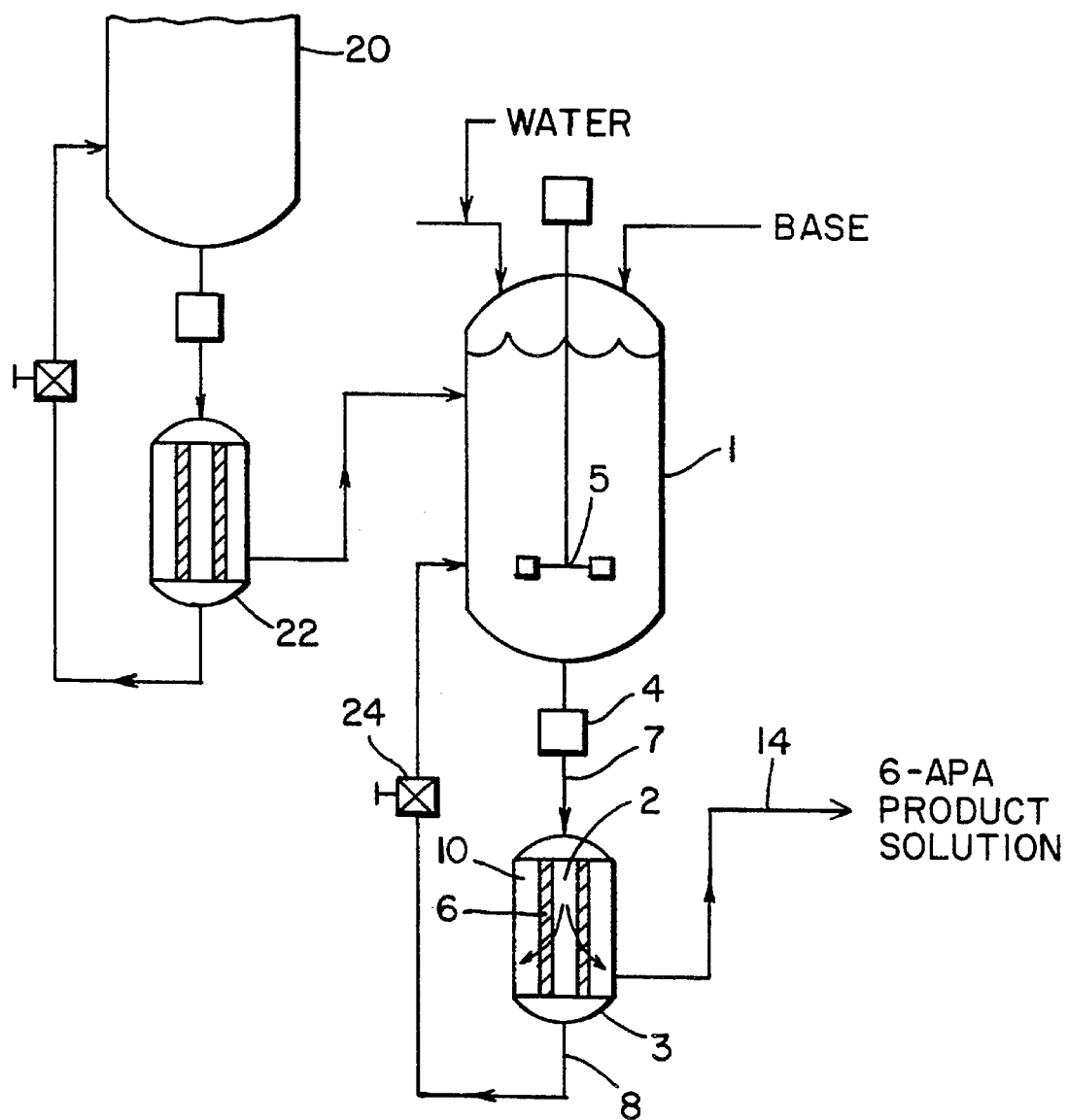
FIG. 2 is a schematic drawing of an apparatus for the practice of an integrated process according to the invention.

FIG. 2 is a schematic of the integrated process.

A PenGK salt solution (Step 5 solution) is transferred to the feed tank 20 for each batch. This solution is circulated through a hydrophilic hollow fiber ultrafiltration membrane module 22 to remove insolubles (BuOAc droplets will not pass through the membrane) and proteinaceous material. The clarified solution (filtrate) is collected in the enzyme reactor tank. The terms "substantially free of" immiscible solvent phase and of proteinaceous contaminants refer to a condition wherein the concentration of both are below the limit of visual detection.

At the start of a typical batch, the enzyme is distributed through the system but is somewhat more concentrated at the lumen surface of the filter membrane 6. The pH and temperature of the PenGK solution are adjusted. The process pump then starts to circulate the PenGK solution through the membrane modules, thereby mixing it with the enzyme.

The enzyme catalyzes the hydrolysis of the PenGK to form the desired product, 6-APA and phenylacetic acid. This acid must be neutralized by titration with a base (ammonium hydroxide) to maintain a constant pH, which is accomplished by a pH controller.

In this process, the enzyme is dissolved in solution; no immobilization is required. The enzyme is separated from the product solution by the ultrafiltration membrane (without any damage to the enzyme) and recycled for another batch.

After a specified period of time, the system is stopped and the valve 24 set to ultrafilter the product solution through the membrane modules 3 to the product solution tank (not shown). The enzyme does not pass through the membrane, and is thus retained for the next batch. After the contents of the process tank and most of the process piping have been filtered through the membrane, a water rinse is used to flush residual product solution through the system. The cycle then starts again.

Significant advantages that obtain from the integrated process using the crude penicillin feed stream include the elimination of the solvent extraction and salt precipitation steps. The elimination of the solvent extraction step reduces the amount of solvent which must be regenerated and therefore the costs associated with this regeneration process. Other savings arise from the elimination of yield losses associated with this extraction. The elimination of the salt precipitation step eliminates the costs associated with potassium acetate and with cooling, which is necessary for complete precipitation.

EXAMPLE 2

Two liters of fluid from step 5 in the standard production process above containing about 1–2% butyl acetate was recirculated through the lumen of a polyacrylamide hollow fiber device. (Sepracor LP Marlboro, Mass.) The fluid contained about 75 g/L of PenGK. A pressure differential of about 13 psi was maintained across the membrane. About 1.6L of filtered fluid was withdrawn from the shell over the course of 20 minutes. The filtered fluid was clear, unlike the step 5 fluid which was hazy. The filtered fluid was delivered to a reactor as described in example 1.

While the invention has been particularly shown and described with reference to preferred embodiments thereof, it will be understood by those skilled in the art that other changes in form and details may be made therein without departing from the spirit and scope of the invention.

I claim:

1. A process for producing 6-aminopenicillanic acid (6-APA) from a 6-acylaminopenicillanic acid (6-AAPA) comprising the steps of:

(a) supplying to a reaction vessel a solution of 6-AAPA or a salt thereof;

(b) supplying a solution of free penicillin acylase to said reaction vessel;

(c) circulating said solution of 6-AAPA and penicillin acylase to produce a homogeneous solution at pH 7.0 to 9.0 and 20° to 40° C.;

(d) continuing circulating said solution until said 6-AAPA is at least 90% converted to a solution of 6-APA;

(e) filtering said solution of 6-APA through a membrane filter until at least 90% of said 6-APA has passed from the first side of said membrane filter to the second side of said membrane filter as a filtrate, while less than 10% of said penicillin acylase has passed from said first side to said second side;

(f) recovering 6-APA from said filtrate; and (g) circulating a retentate containing said free penicillin acylase back to said reaction vessel.

2. A process according to claim 1 further characterized in that step (b) is carried out by circulating said solution of 6-AAPA from said reaction vessel over said first side of said membrane filter, whereby said solution of 6-AAPA is brought into contact with a penicillin acylase in solution.

3. A process according to claim 1 wherein said solution of 6-APA is filtered through an anisotropic membrane of polyacrylonitrile having a cutoff of 10 to 100 kdaltons.

4. A process according to claim 3 wherein said solution is filtered through a hollow fiber membrane.

5. A process according to claim 3 wherein solution is filtered through a flat sheet membrane.

6. A process according to claim 1 wherein said 6-AAPA solution is a 5 to 10% solution of potassium benzyl penicillin.

7. A process according to claim 1 wherein said 6-AAPA solution is a 5 to 10% solution of phenoxymethyl penicillin.

8. A process according to claim 6 wherein said solution of potassium benzyl penicillin is circulated at about pH 7.5 to 8.5 and about 25° to about 30° C. in the presence of about 10 to about 2000 units of penicillin acylase per gram of potassium benzyl penicillin.

9. A process according to claim 7 wherein said solution of phenoxymethyl penicillin is circulated at about pH 7.5 to 8.5 and about 25° to about 30° C. in the presence of about 10 to about 2000 units of penicillin acylase per gram of phenoxymethyl penicillin.

10. An integrated process for producing 6-aminopenicillanic acid (6-APA) from a fermentation broth comprising the steps of:

(a) acidifying a clarified fermentation broth containing a 6-acylaminopenicillanic acid (6-AAPA) or salt thereof;

(b) extracting said 6-AAPA into a suitable water-immiscible organic solvent;

(c) extracting said 6-AAPA from said water immiscible organic solvent into an alkaline aqueous solution;

(d) circulating said alkaline aqueous solution of 6-AAPA through a first hydrophilic membrane filter having a cutoff of 10 to 100 kdaltons to produce a clear aqueous first filtrate wherein concentrations of water-immiscible solvent phase and proteinaceous contaminants are below the limit of visual detection;

(e) combining said clear aqueous first filtrate with an aqueous solution of free penicillin acylase at pH 7.0 to 9.0 and at 20° to 40° to provide a homogeneous solution of 6-AAPA and penicillin acylase;

(f) allowing said 6-AAPA and penicillin acylase to react until said solution of 6-AAPA is at least 90% converted to a solution of 6-APA;

(g) filtering said solution of 6-APA through a membrane filter whereby at least 90% of said 6-APA in said solution is passed through said membrane as a second filtrate while less than 10% of said penicillin acylase passes through said membrane; and (h) recovering 6-APA from said second filtrate.

11. A process according to claim 10 wherein said water-immiscible solvent is chosen from the group consisting of butyl acetate, amyl acetate and methyl isobutyl ketone.

12. A process according to claim 10 wherein said first hydrophilic membrane is an anisotropic polyacrylonitrile hollow fiber ultrafiltration membrane.

13. A process according to claim 10 wherein said 6-acylaminopenicillanic acid or salt thereof is potassium benzyl penicillin.

14. A process according to claim 10, wherein said 6-acylaminopenicillanic acid or salt thereof is phenoxymethyl penicillin.

15. A process according to claim 10 wherein said clear aqueous filtrate is a 5 to 10% solution of potassium benzyl penicillin which is then combined with about 10 to 2,000 units of penicillin acylase per gram of potassium benzyl penicillin at about pH 7.5 to 8.5 and about 25° to about 30° C.

16. A process according to claim 10 wherein said clear aqueous filtrate is a 5 to 10% solution of phenoxymethyl penicillin which is then combined with about 10 to 2,000 units of penicillin acylase per gram of phenoxymethyl penicillin at about pH 7.5 to 8.5 and about 25° to about 30° C.

17. A process according to claim 1 wherein said solution of 6-AAPA and penicillin acylase is circulated within said reaction vessel.

18. A process according to claim 1 wherein said solution of 6-AAPA and penicillin acylase is circulated between said reaction vessel and said first side of said filter.

* * * * *